US011826202B2

(12) United States Patent
Li

(10) Patent No.: US 11,826,202 B2
(45) Date of Patent: Nov. 28, 2023

(54) ULTRASOUND ELASTICITY MEASUREMENT DEVICE AND METHOD

(71) Applicant: SHENZHEN MINDRAY BIO-MEDICAL ELECTRONICS CO., LTD., Guangdong (CN)

(72) Inventor: Shuangshuang Li, Shenzhen (CN)

(73) Assignee: Shenzhen Mindray Bio-Medical Electronics Co., Ltd., Shenzhen (CN)

( * ) Notice: Subject to any disclaimer, the term of this patent is extended or adjusted under 35 U.S.C. 154(b) by 0 days.

(21) Appl. No.: 17/082,898

(22) Filed: Oct. 28, 2020

(65) Prior Publication Data

US 2021/0038196 A1 Feb. 11, 2021

Related U.S. Application Data

(63) Continuation of application No. PCT/CN2018/085179, filed on Apr. 28, 2018.

(51) Int. Cl.
*A61B 8/08* (2006.01)
*A61B 8/00* (2006.01)

(52) U.S. Cl.
CPC ............ *A61B 8/485* (2013.01); *A61B 8/4444* (2013.01); *A61B 8/461* (2013.01); *A61B 8/5207* (2013.01)

(58) Field of Classification Search
CPC ....... A61B 8/485; A61B 8/4444; A61B 8/461; A61B 8/5207
See application file for complete search history.

(56) References Cited

U.S. PATENT DOCUMENTS

2003/0009101 A1\* 1/2003 Sunagawa .......... A61B 5/02007
600/437
2005/0085728 A1\* 4/2005 Fukuda ................ G01N 29/227
600/449
(Continued)

FOREIGN PATENT DOCUMENTS

CN 103347450 A 10/2013
CN 103800038 A 5/2014
(Continued)

OTHER PUBLICATIONS

Translated Azuma (JP 2012249776 A) (Year: 2012).\*
(Continued)

*Primary Examiner* — Katherine L Fernandez
*Assistant Examiner* — Brooke Lyn Klein
(74) *Attorney, Agent, or Firm* — Sheppard Mullin Richter & Hampton LLP

(57) ABSTRACT

An ultrasound elasticity measurement device includes an ultrasound probe. The ultrasound probe includes a vibrator and a transducer. The ultrasound elasticity measurement device further includes a vibration controller, a transmission/receiving controller and a data processor. When simultaneously performing the strain detection and the vibration elasticity detection, the vibration controller generates a vibration control sequence and transmits the same to the vibrator. The ultrasound probe vibrates when driven by the vibrator, and transmits ultrasound waves to the biological tissue and receives the ultrasound echoes, so as to obtain the ultrasound echo data for strain detection and the ultrasound echo data for vibration elasticity detection. The data processor calculates the strain elasticity result according to the ultrasound echo data for strain detection calculates the vibration elasticity result according to the ultrasound echo data for vibration elasticity detection, thereby realizing (Continued)

simultaneously to strain elasticity imaging and the vibration elasticity measurement.

12 Claims, 9 Drawing Sheets

(56) References Cited

U.S. PATENT DOCUMENTS

| | | | |
|---|---|---|---|
| 2011/0096958 A1* | 4/2011 | Fukumoto | A61B 8/08 |
| | | | 382/106 |
| 2011/0237939 A1* | 9/2011 | Melamed | G06T 5/50 |
| | | | 600/425 |
| 2013/0261453 A1* | 10/2013 | Tamura | A61B 8/488 |
| | | | 600/438 |
| 2013/0317361 A1 | 11/2013 | Tabaru et al. | |
| 2014/0276049 A1 | 9/2014 | Doherty et al. | |
| 2015/0164473 A1* | 6/2015 | Kim | G01S 15/8925 |
| | | | 600/443 |
| 2015/0209013 A1 | 7/2015 | Tsymbalenko | |
| 2017/0333005 A1* | 11/2017 | Chen | A61B 8/14 |
| 2018/0296181 A1* | 10/2018 | Zhai | A61B 8/485 |
| 2019/0083067 A1* | 3/2019 | Kim | A61B 8/085 |
| 2019/0183461 A1* | 6/2019 | Sonoyama | G01S 7/52042 |
| 2019/0254639 A1* | 8/2019 | Yin | A61B 8/085 |

FOREIGN PATENT DOCUMENTS

| | | | |
|---|---|---|---|
| CN | 105662473 A | | 6/2016 |
| CN | 205458781 U | | 8/2016 |
| CN | 107106120 A | | 8/2017 |
| CN | 107684457 A | | 2/2018 |
| EP | 2113202 A1 | | 11/2009 |
| JP | 2012249776 | * | 12/2012 |
| WO | 2018/037859 A1 | | 3/2018 |

OTHER PUBLICATIONS

PCT International Search Report and the Written Opinion dated Dec. 11, 2018, issued in related International Application No. PCT/CN2018/085179, with English translation (12 pages).

PCT International Preliminary Report on Patentability dated Nov. 12, 2020, issued in related International Application No. PCT/CN2018/085179, with English translation (10 pages).

First Search dated Sep. 27, 2021, issued in related Chinese Application No. 201880018217.1 (2 pages).

Supplementary Search dated Apr. 18, 2022, issued in related Chinese Application No. 201880018217.1 (2 pages).

* cited by examiner

ULTRASOUND ELASTICITY MEASUREMENT DEVICE AND METHOD

CROSS-REFERENCE TO RELATED APPLICATION

This application is a continuation application of International Patent Application No. PCT/CN2018/085179, filed with the China National Intellectual Property Administration (CNIPA) of People's Republic of China on Apr. 28, 2018, and entitled "ULTRASOUND-BASED ELASTICITY MEASUREMENT DEVICE AND METHOD". The entire content of the above-identified application is incorporated herein by reference.

TECHNICAL FIELD

The present disclosure relates to medical devices, in particular to ultrasound elasticity measurement devices.

BACKGROUND

Ultrasound elasticity imaging is one of the hot spots in clinical research in recent years. Since it mainly presents the elasticity or hardness of tissues, it has been used more and more in the auxiliary detection, discrimination of benign and malignant and evaluation of prognosis recovery, etc. of the tissue cancer lesions.

The ultrasound elasticity imaging mainly images elasticity-related parameters in the region of interest, thereby presenting the hardness of the tissue. In the past two decades, many different elasticity imaging methods have been developed, such as the quasi-static elasticity imaging based on strain caused by the probe pressing the tissue, and the vibration elasticity imaging based on the shear waves generated by an external vibration, etc.

The quasi-static elasticity imaging is also called strain elasticity imaging, in which a certain deformation may be generated by pressing the tissue with a convex array or linear array multi-element probe, the strain may be detected, and the parameters related to tissue elasticity such as strain or strain rate may be calculated and imaged. With the quasi-static elasticity imaging, the elasticity difference between different tissues may be represented indirectly. However, since the strain parameters are sensitive to pressure, the pressure applied by the probe in this method needs to be as uniform and stable as possible, which leads to higher requirements on the operator's technique. In addition, because the pressures in the operation are difficult to keep consistent, the repeatability and stability of the imaging are also difficult to guarantee.

In the vibration elasticity imaging method, a vibrator may be used to drive the single-element probe to vibrate to generate the shear waves that propagate in the depth direction in the tissue, and the propagation of the shear wave may be detected so as to calculate the tissue elasticity parameter that can represents the hardness of the region of interest. However, this method can only give the average elasticity results of the region of interest, but cannot achieve the true imaging. Therefore, the elasticity distribution in the region of interest cannot be obtained.

SUMMARY

In one embodiment, an ultrasound elasticity measurement device is provided, which may include:

an ultrasound probe including a vibrator and a transducer, where, the transducer includes multiple elements; the elements transmit ultrasound waves to the biological tissue in the region of interest and receive the ultrasound echoes returned from the biological tissue to obtain the ultrasound echo data for strain detection and the ultrasound echo data for vibration elasticity detection in a mode of simultaneously performing the strain detection and the vibration elasticity detection; and the vibrator obtains a vibration control sequence and drives the transducer to vibrate according to the vibration control sequence, where the vibration causes the biological tissue to deform when the ultrasound probe contacts the biological tissue and generates a shear wave that propagates to inside of the biological tissue;

A vibration controller that is connected with the vibrator and configured to generate a vibration control sequence in the mode of simultaneously performing the strain detection and the vibration elasticity detection and output the vibration control sequence to the vibrator;

a transmitting/receiving controller that is configured to generate a transmitting sequence group and a receiving control signal and output the transmitting sequence group and the receiving control signal to the ultrasound probe, where the transmitting sequence group controls part or all of the multiple elements to transmit the ultrasound waves to the biological tissue in the region of interest and the receiving control signal controls part or all of the multiple elements to receive echoes of the ultrasound waves; and a data processor that is configured to calculate a strain elasticity result according to the ultrasound echo data for strain detection and calculate a vibration elasticity result according to the ultrasound echo data for vibration elasticity detection.

In one embodiment, an ultrasound elasticity measurement device is provided, which may include:

an ultrasound probe including a vibrator and a transducer, where, the transducer includes multiple elements; the elements transmit ultrasound waves to a biological tissue in a region of interest in a strain detection mode and receive an ultrasound echo data for strain detection returned from the biological tissue, and transmit ultrasound waves to the biological tissue in the region of interest in a vibration elasticity detection mode and receive an ultrasound echo data for vibration elasticity detection returned from the biological tissue; and the vibrator obtains a vibration control sequence and drives the transducer to vibrate according to the vibration control sequence, where the vibration causes the biological tissue to deform when the ultrasound probe contacts the biological tissue and generates a shear wave that propagates to inside of the biological tissue;

a vibration controller that is connected with the vibrator and configured to generate at least a vibration control sequence for vibration elasticity detection in the vibration elasticity detection mode and output the vibration control sequence for vibration elasticity detection to the vibrator;

a transmitting/receiving controller that is configured to generate a transmitting sequence group and a receiving control signal and output the transmitting sequence group and the receiving control signal to the ultrasound probe, where the transmitting sequence group controls part or all of the multiple elements to transmit the ultrasound waves to the biological tissue in the region of interest and the receiving control signal controls part or all of the multiple elements to receive echoes of the ultrasound waves;

a data processor that is configured to calculate a strain elasticity result according to the ultrasound echo data for strain detection and calculate a vibration elasticity result according to the ultrasound echo data for vibration elasticity detection; and a display device that is configured to simultaneously display the strain elasticity result and the vibration elasticity result on a display interface when a user inputs an instruction for simultaneous display.

In one embodiment, an ultrasound elasticity measurement method is provided, which may include:

receiving an instruction for simultaneously performing a strain detection and a vibration elasticity detection input by a user to enter a mode of simultaneously performing the strain detection and the vibration elasticity detection;

outputting a vibration control sequence to a vibrator;

the vibrator driving a transducer of an ultrasound probe to vibrate according to the vibration control sequence, where the vibration causes a biological tissue to deform when the ultrasound probe contacts the biological tissue and generate a shear wave that propagate to inside of the biological tissue;

outputting a transmitting sequence group and a receiving control signal to the ultrasound probe;

controlling part or all of multiple elements of the ultrasound probe according to the transmitting sequence to transmit an ultrasound wave to the biological tissue in a region of interest and controlling part or all of the multiple elements according to the receiving control signal to receive echoes of the ultrasound wave to obtain an ultrasound echo data for strain detection and an ultrasound echo data for vibration elasticity detection; and the data processor calculating a strain elasticity result according to the ultrasound echo data for strain detection and calculating a vibration elasticity result according to the ultrasound echo data for vibration elasticity detection.

In one embodiment, an ultrasound elasticity measurement method is provided, which may include a strain detection step, a vibration elasticity detection step and a simultaneously displaying step.

The strain detection step may include:

receiving an instruction for performing a strain detection input by a user to enter a strain detection mode;

outputting a transmitting sequence group and a receiving control signal to an ultrasound probe when a biological tissue is deformed;

controlling part or all of multiple elements of the ultrasound probe to transmit an ultrasound wave to the biological tissues in a region of interest according to the transmitting sequence group and controlling part or all of the multiple elements to receive the echoes of the ultrasound wave according to the receiving control signal to obtain an ultrasound echo data for strain detection; and a data processor calculating a strain elasticity result according to the ultrasound echo data for strain detection.

The vibration elasticity detection step may include:

receiving an instruction for performing a vibration elasticity detection input by the user to enter a vibration elasticity detection mode;

outputting a vibration control sequence for vibration elasticity detection to the vibrator;

the vibrator driving a transducer of the ultrasound probe to vibrate according to the vibration control sequence for vibration elasticity detection, wherein the vibration generates a shear wave that propagates to inside of the biological tissue;

outputting a transmitting sequence group and a receiving control signal to the ultrasound probe;

controlling part or all of the multiple elements of the ultrasound probe to transmit an ultrasound wave to the biological tissues in the region of interest according to the transmitting sequence group, and controlling part or all of the multiple elements to receive echoes of the ultrasound waves according to the receiving control signal to obtain an ultrasound echo data for vibration elasticity detection; and the data processor calculating a vibration elasticity result according to the ultrasound echo data for vibration elasticity detection; and The simultaneous displaying step may include:

receiving an instruction for simultaneous displaying input by the user; and displaying the strain elasticity result and the vibration elasticity result simultaneously on a display interface.

In one embodiment, an ultrasound elasticity measurement method is provided, which may include: generating a deformation in a biological tissue; transmitting ultrasound waves to the biological tissue through an ultrasound probe and receiving ultrasound echoes to obtaining ultrasound echo data for strain detection before and after the deformation is generated; calculating a strain elasticity result according to the ultrasound echo data for strain detection; generating in the biological tissue a shear wave propagating to inside of the biological tissue; transmitting an ultrasound wave to the biological tissue through the ultrasound probe to track a propagation of the shear wave and receiving ultrasound echoes to obtain an ultrasound echo data for vibration elasticity detection; calculating a vibration elasticity result according to the ultrasound echo data for vibration elasticity detection; and simultaneously displaying the strain elasticity result and the vibration elasticity result.

In the embodiments of the present disclosure, a vibrator may be used to drive the ultrasound probe to vibrate with a specific law. On the one hand, instead of manual operation, the vibrator may be used to drive the ultrasound probe to vibrate so as to achieve the strain elasticity imaging. On the other hand, the vibrator may be used to drive the ultrasound probe to vibrate to generate the shear wave to achieve the vibration elasticity measurement. Therefore, the elasticity distribution of the tissue in the target area can be provided, and the quantitative elasticity measurement of the tissue in a specific area can be achieved, thereby achieving the strain elasticity measurement and the vibration elasticity measurement simultaneously. In addition, the methods in the present disclosure do not rely on the pressing operations of human hand, therefore the image stability and repeatability are better.

DETAILED DESCRIPTION

The present disclosure will be described in detail below with reference to the embodiments and drawings, where similar elements in different embodiments are designated with similar reference numbers. In the following embodiments, many details are described so as to facilitate the understanding to the present disclosure. However, those skilled in the art will easily recognize that some of the features may be omitted in different situations, or may be replaced by other elements, materials or methods. In some cases, some operations are not shown or described in the specification, which is to avoid the core part of the present disclosure being overwhelmed by too many descriptions. For those skilled in the art, detailed description of these operations is not necessary. They can fully understand these operations according to the description in the specification and general technical knowledge in the field.

In addition, the features, operations or characteristics described in the specification may be combined in any appropriate manner to form various embodiments. Furthermore, the steps or actions in the described methods may also be changed or adjusted in the order in a manner obvious to those skilled in the art. Therefore, the various orders in the description and drawings are only for clearly describing a certain embodiment, but not meant to be a necessary order unless otherwise stated that a certain order must be followed.

The serial numbers for the elements in the present disclosure, such as "first", "second", etc., are only used to distinguish the described objects, but do not have any order or technical meaning. The "connection" and "coupling" as used herein, unless otherwise specified, will include both direct and indirect connection (coupling).

Figure 1:
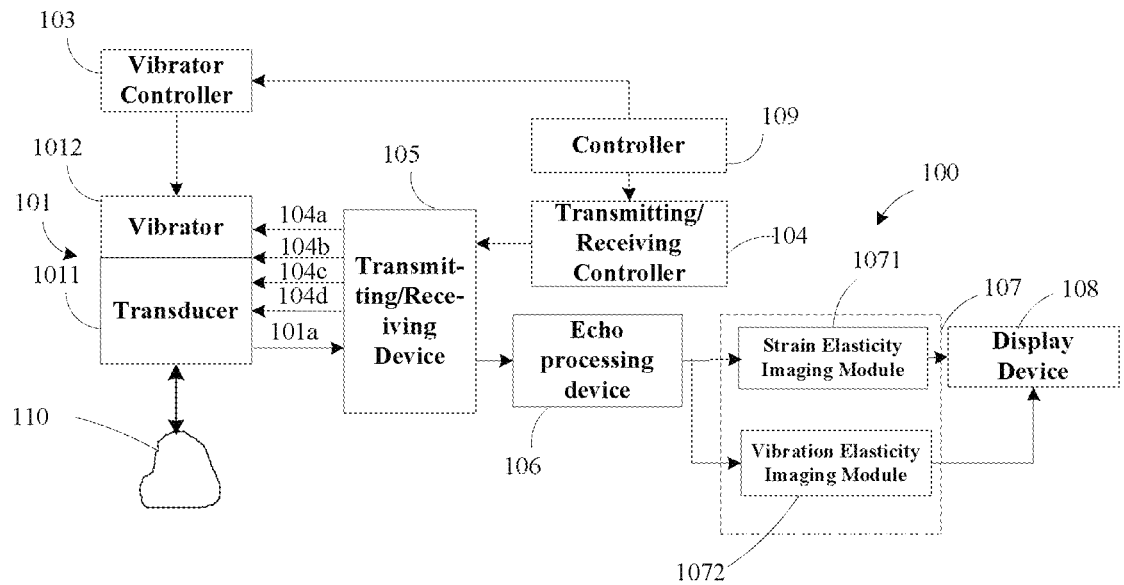
FIG. 1 is a schematic block diagram of an ultrasound elasticity measurement device in one embodiment.

Referring to FIG. 1, in one embodiment, the ultrasound elasticity measurement device 100 may include an ultrasound probe 101, a vibration controller 103, a transmitting/receiving controller 104, a transmitting/receiving device 105, an echo processing device 106, a data processor 107, a display device 108 and a controller 109. The transmitting/receiving controller 104 may be connected to the ultrasound probe 101 through the transmitting/receiving device 105. The ultrasound probe 101 may be connected to the echo processing device 106 through the transmitting/receiving device 105. The output end of the echo processing device 106 may be connected to the data processor 107. The output end of the data processor 107 may be connected to the display device 108. The ultrasound probe 101 may include a transducer 1011 and a vibrator 1012.

The vibrator 1012 may be mounted on the ultrasound probe 101, such as on the housing of the ultrasound probe 101. Alternatively, the vibrator 1012 may be mounted in the housing of the ultrasound probe 101 so as to be assembled with the transducer and other probe components into an integrated ultrasound probe. The vibrator may receive the vibration control sequence from the vibration controller 103 and drive the transducer to vibrate according to the vibration control sequence. For example, the vibrator itself may vibrate according to the vibration control sequence so as to drive the transducer to vibrate. Alternatively, the vibrator itself may not vibrate, while the telescopic or rotating part thereof move according to the vibration control sequence so as to drive the transducer to vibrate. The vibration may cause the deformation of the biological tissue when the ultrasound probe contacts the biological tissue, thereby generating a shear wave that propagates in the biological tissue in the depth direction of the tissue. The driving process of the vibrator 1012 completed according to one vibration control sequence may be called one vibration. When the vibration controller 103 outputs the next vibration control sequence, the vibrator 1012 may start the next vibration.

The vibration controller 103 may be connected with the vibrator, and used to generate the vibration control sequence. The vibration control sequence may include the parameters such as waveform, frequency, amplitude and duration, etc.

The transducer 1011 may include multiple elements arranged in an array. The multiple elements may be arranged in a row to form a linear array, or arranged in a two-dimensional matrix to form a matrix array. The multiple elements may also form a convex array. The elements may transmit ultrasound waves according to the excitation electrical signal, or transform the received ultrasound waves into electrical signals. Therefore, the element may be used for transmitting the ultrasound waves to the biological tissue in the region of interest, and may also be used for receiving the ultrasound echoes returned from the tissue. When performing the ultrasound testing, it may be controlled by the transmitting sequence group and the receiving control signals which elements will be used in the transmitting of the ultrasound waves and which elements will be used in the receiving of the ultrasound echoes. Alternatively, the element may be controlled to both transmit the ultrasound waves and receive the ultrasound echoes in a time division manner. The elements participating in the ultrasound transmitting may be excited by the electrical signals at the same time, so as to transmit the ultrasound waves at the same time. Alternatively, the elements participating in the ultrasound transmitting may be excited by the electrical signals with a certain time interval, so as to continuously transmit the ultrasound waves with a certain time interval.

In this embodiment, under the mode of simultaneously performing the strain detection and the vibration elasticity detection, part or all of the multiple elements may transmit the ultrasound waves to the biological tissue in the region of interest. According to the transmitting sequence group, the transmitted ultrasound waves may be used for strain detection, or be used for vibration elasticity detection, or be used for both detections. Part or all of the multiple elements may receive the ultrasound echoes. The received ultrasound echoes may be used for the strain detection and the vibration elasticity detection.

Figure 2A:
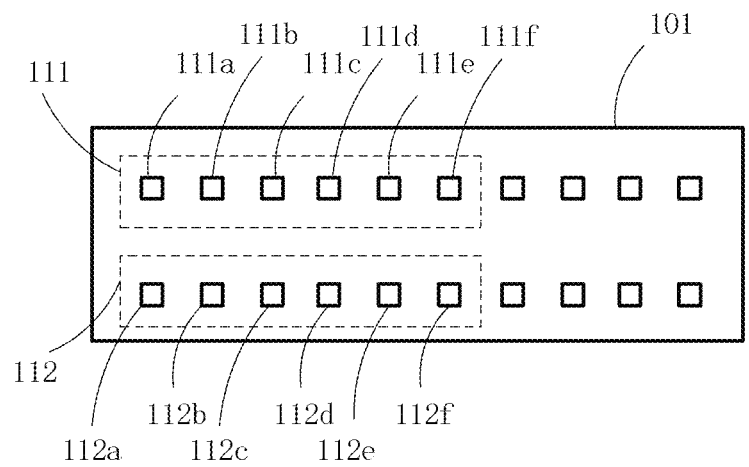
FIG. 2a and FIG. 2b are schematic cross-sectional views of the ultrasound probe.

FIG. 2*a* is a schematic cross-sectional view of the ultrasound probe. The multiple elements may be arranged in a two-dimensional matrix on the ultrasound probe 101 to form a matrix array. The row of elements in the upper box 111 may be used for transmitting the ultrasound waves, where the elements 111*a*, 111*b*, 111*c*, 111*d*, 111*e* and 111*f* may be used for transmitting the ultrasound waves for detecting the deformation of the biological tissue and the elements 111*c* and 111*d* may be used for transmitting the ultrasound waves for detecting the shear wave. The row of elements in the box 112 below may be used for receiving the ultrasound echoes, where the elements 112*a*, 112*b*, 112*c*, 112*d*, 112*e* and 112*f* may be used for receiving the ultrasound waves for detecting the deformation of the biological tissue and the elements 112*c* and 112*d* may be used for receiving the ultrasound echoes for detecting the shear wave. Of course, in other embodiments, the elements 111*a*, 111*b*, 111*c* and 111*d* may be used for transmitting the ultrasound waves for detecting the deformation of the biological tissue and the elements 112*a*, 112*b*, 112*c* and 112*d* may be used for receiving the ultrasound waves for detecting the deformation of the biological tissue, while the elements 111*e* and 111*f* may be used for transmitting the ultrasound waves for detecting the shear wave and the elements 112*e* and 112*f* may be used for receiving the ultrasound waves for detecting the shear wave.

Figure 2B:
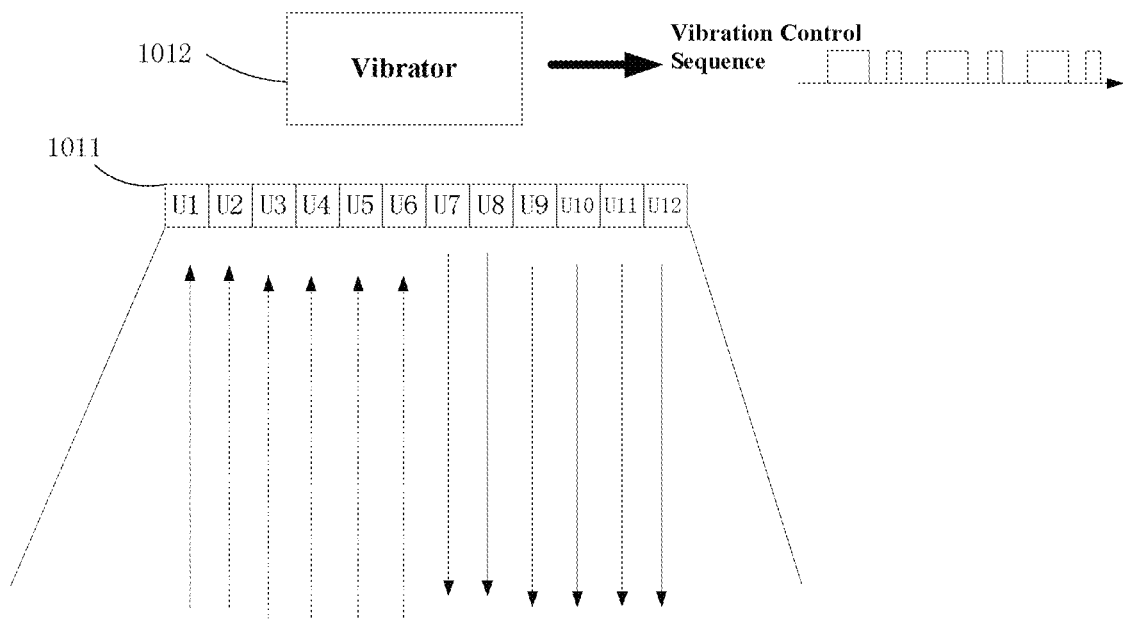

As shown in FIG. 2*b*, the multiple elements may also be arranged in a line array, and part or all of the multiple elements in the transducer 1011 may be used to transmit the ultrasound waves or receive the ultrasound echoes. For example, at the first time, part or all of the elements may be used to transmit the ultrasound beams. For example, the elements U1-U6 may be used for transmitting. At the second time, part or all of the elements may be used to receive the echoes of the ultrasound beams. For example, the elements U7-U12 may be used for receiving. Furthermore, the elements used for transmitting or receiving at different times may overlap. For example, at the first time, the elements U1-U9 may be used for transmitting, and at the second time, the elements U4-U12 may be used for receiving.

The transmit/receive controller 104 may generate the transmitting sequence group and the receiving control signals. The transmitting sequence group may control part or all of the multiple elements to transmit the ultrasound waves to the biological tissue in the region of interest. The parameter of the transmitting sequence group may include the number of the elements participating in the transmitting and the ultrasound transmitting parameters (such as the amplitude, frequency, number of transmitting, interval of transmitting, angle of transmitting, wave type, etc.). The receiving control signal may control part or all of the multiple elements to receive the echoes of the ultrasound wave. The parameter of the receiving control signal may include the number of the elements participating in the receiving and the receiving parameters of the echoes (such as angle of receiving, depth, etc.). For different purposes of the ultrasound echoes or different images generated by the ultrasound echoes, the transmitting parameters in the transmitting sequence group and the receiving parameters in the receiving control signal may be different.

In this embodiment, the transmitting sequence group output from the transmitting/receiving controller 104 to the ultrasound probe may include a first transmitting sequence group 104*a* and a second transmitting sequence group 104*c*. The first transmitting sequence group may control the corresponding elements to transmit the ultrasound waves for detecting the deformation of the biological tissue. The second transmitting sequence group may control the corresponding elements to transmit the ultrasound waves for detecting the shear wave. The receiving control signal output by the transmitting/receiving controller 104 to the ultrasound probe may include a first receiving control signal 104*b* and a second receiving control signal 104*d*. The first receiving control signal may control the corresponding elements to receive the ultrasound echoes for the strain detection. The second receiving control signal may control the corresponding elements to receive the ultrasound echoes for the vibration elasticity detection. In the first and second transmitting sequence groups, the position and number of the elements for transmitting the ultrasound waves and the transmitting parameters may be respectively set. In the first and second receiving control signals, the position and number of the elements for receiving the echoes and the receiving parameters may be respectively set. According to the transmitting sequence group and receiving control signal, the at least part of the elements of the ultrasound probe may be used to transmit the ultrasound waves and at least part of the elements may be used to receive the ultrasound echoes. Some of the elements used for transmitting the ultrasound waves may transmit the ultrasound wave for detecting the deformation of the biological tissue and some may transmit the ultrasound waves for detecting the shear wave. The elements for transmitting the former ultrasound waves and the latter ultrasound waves may or may not overlap. Some of the elements used for receiving the ultrasound echoes may receive the ultrasound echoes for the strain detection, and some may receive the ultrasound echoes for the vibration elasticity detection. The elements for receiving the former echoes and the latter echoes may or may not overlap.

The transmitting/receiving device 105 may be connected between the ultrasound probe and the transmitting/receiving controller 104 and the echo processing device 106, and may transmit the transmitting sequence group generated by the transmitting/receiving controller 104 to the ultrasound probe 101 and transmit the ultrasound echoes 101*a* received by the ultrasound probe 101 to the echo processing device 104.

The controller 109 may be connected to the transmitting/receiving controller 104 and the vibration controller 103, and may control the output sequence of the transmitting/receiving controller 104 and the vibration controller 103. When the controller 109 receives the instruction of the user for performing the strain detection and the vibration elasticity detection simultaneously, the controller 109 may control the vibration controller 103 to output a vibration control sequence. The vibrator may start one vibration according to the vibration control sequence, and the controller 109 may control the transmitting/receiving controller 104 to output the first transmitting sequence group and the first receiving control signal, the second transmitting sequence group and the second receiving control signal. The first transmitting sequence group and the first receiving control signal and the second transmitting sequence group and the second receiving control signal may be output simultaneously or sequentially. For example, the first transmitting sequence group and the first receiving control signal may be output first, and then the second transmitting sequence group and the second receiving control signal may be output. The ultrasound probe may transmit the ultrasound waves and receive the echoes according to the first transmitting sequence group and the first receiving control signal and the second transmitting sequence group and the second receiving control signal. In this case, the ultrasound probe may simultaneously or sequentially transmitting the ultrasound waves for the strain detection and the ultrasound waves for shear wave detection for one vibration. In some embodiments, the ultrasound probe may transmit the ultrasound waves for the strain detection or the ultrasound waves for the shear wave detection for different vibrations. For example, when the controller 109 receives the instruction of the user for simultaneously performing the strain detection and vibration elasticity detection, the controller 109 may control the vibration controller 103 to output one vibration control sequence, and the vibrator may start the first vibration according to the vibration control sequence. The controller 109 may control the transmitting/receiving controller 104 to output the first transmitting sequence group and the first receiving control signal. The ultrasound probe may transmit the ultrasound waves and receive the echoes according to the first transmitting sequence group and the first receiving control signal. Thereafter, the controller 109 may control the vibration controller 103 to output one vibration control sequence again, and the vibrator may start the second vibration according to the vibration control sequence. The controller 109 may control the transmitting/receiving controller 104 to output the second transmitting sequence group and the second receiving control signal. The ultrasound probe may transmit the ultrasound waves and receive the echoes according to the second transmitting sequence group and the second receiving control signal. Alternatively, the ultrasound probe may also transmit the ultrasound waves for the vibration elasticity detection for the first vibration and transmit the ultrasound waves for the strain detection for the second vibration. In addition, the detection may also be carried out sequentially and cyclically, so as to achieve real-time update of the detection results.

Figure 2C:
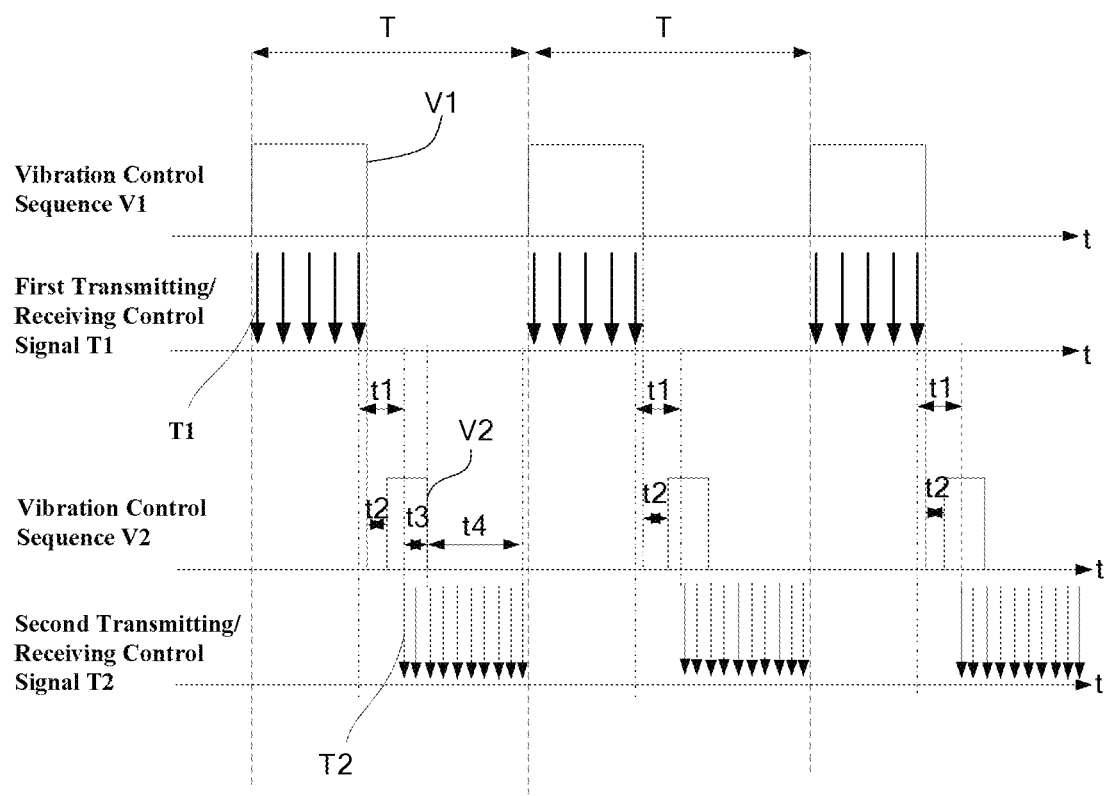
FIGS. 2c-2e are sequence diagrams for simultaneously performing the strain elasticity detection and the vibration elasticity detection in one embodiment.

As shown in FIG. 2c, in the mode of simultaneously performing the strain detection and the vibration elasticity detection, within one period T, the controller 109 may first control the vibration controller 103 to output the vibration control sequence V1, and the vibrator may drive the transducer to vibrate for the strain detection according to the vibration control sequence V1. As an illustrative example, a square wave is used in the figure to represent the vibration control sequence. The vibration control sequence may also be a sine wave, a triangle wave, etc. After controlling the vibration controller 103 to output the vibration control sequence V1, the controller 109 may control the transmitting/receiving controller to output the first transmitting/receiving control signal T1 (the transmitting/receiving control signal herein may include the transmitting sequence group and the receiving control signal). The transducer may transmit the first ultrasound wave for the strain detection within a first predetermined time period and receive the echoes of the first ultrasound wave according to the first transmitting/receiving control signal T1 to obtain the first ultrasound echo data for the strain detection. Thereafter, the controller 109 may control the vibration controller 103 to output the vibration control sequence V2, and the vibrator may drive the transducer to vibrate for the vibration elasticity detection according to the vibration control sequence V2. After controlling the vibration controller 103 to output the vibration control sequence V2, the controller 109 may control the transmitting/receiving controller to output the second transmitting/receiving control signal T2, and the transducer may transmit the second ultrasound wave for the vibration elasticity detection within the second predetermined time period and receive the echoes of the second ultrasound wave according to the second transmitting/receiving control signal T2 to obtain the second ultrasound echo data for the vibration elasticity detection. In the embodiments, the ultrasound transmitting frequencies set by the first and second transmitting/receiving control signals may be the same or different. There may be a time interval t2 between the vibration control sequence V1 and the vibration control sequence V2. There may be a time interval t1 between the first transmitting/receiving control signal T1 and the second transmitting/receiving control signal T2. The first predetermined time period may be the same as or different from the time period in which the transducer is vibrated for the strain detection. The second predetermined time period may be the third predetermined time period t3 after the transducer starts to vibrate for the vibration elasticity detection plus the fourth predetermined time period t4 after the end of the vibration, that is, after the end of the vibration according to the vibration control sequence V2, the ultrasound transmitting and receiving according to the second transmitting/receiving control signal T2 will still last for a period of time. In some embodiments, in one cycle, the duration of the ultrasound transmitting and receiving according to the second transmitting/receiving control signal is greater than the duration of the ultrasound transmitting and receiving according to the first transmitting/receiving control signal.

Figure 2D:
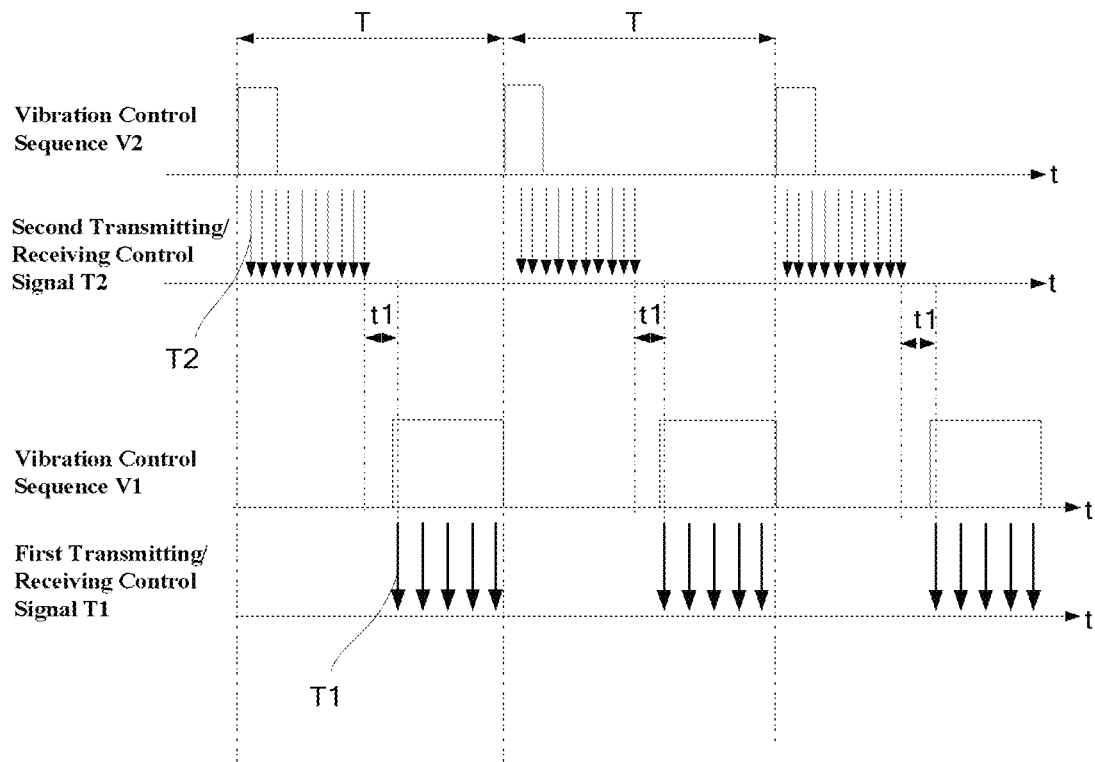

In another embodiment, in one cycle T, the vibration elasticity detection may be performed first, and then the strain detection may be performed, as shown in FIG. 2d.

Figure 2E:
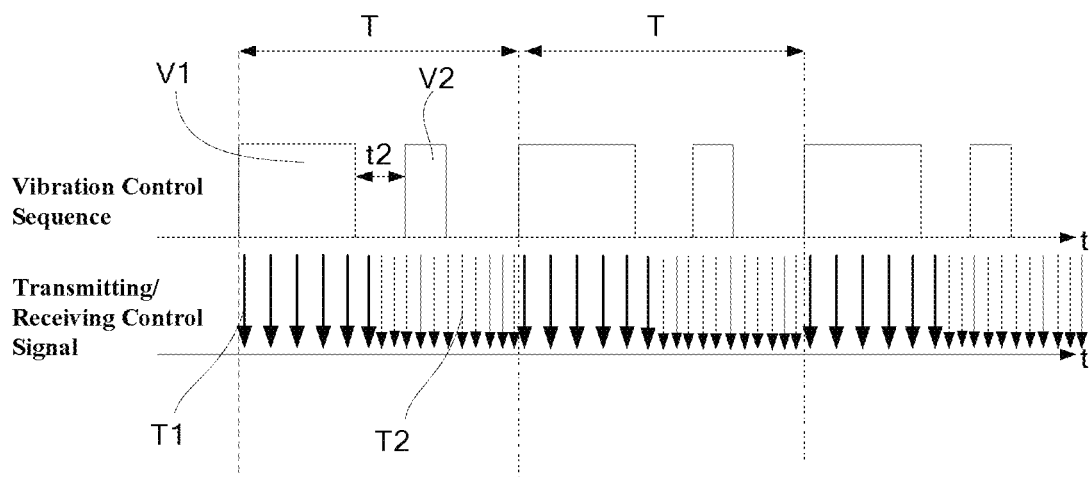

In some embodiments, as shown in FIG. 2e, there may be a time interval t2 between the vibration control sequence V1 and the vibration control sequence V2, and there may be no time interval between the first transmitting/receiving control signal T1 and the second transmitting/receiving control signal T2.

In some embodiments, the controller 109 may also control the switching of the transmitting/receiving device 103, so as to transmit the transmitting sequence group of the transmitting/receiving controller 104 to the ultrasound probe 101 and transmit the ultrasound echo data received by the ultrasound probe 101 to the echo processing device 106. Those skilled in the art should understand that the controller 109 may also control other components in the ultrasound elasticity measurement device 100.

The echo processing device 106 may process the ultrasound echo data, such as filtering, amplifying and beam forming, etc. The ultrasound echo data herein may include both the ultrasound echo data used for the strain detection and the ultrasound echo data for the vibration elasticity detection.

The data processor 107 may receive the echo signal processed by the echo processing device 106, and obtain the desired parameters or images with related algorithms. In the embodiments of the present disclosure, the data processor 107 may include a strain elasticity imaging module 1071 and a vibration elasticity imaging module 1072. The strain elasticity imaging module 1071 may calculate the strain-type elasticity result according to the ultrasound echo data for the strain detection. The strain-type elasticity result may be, for example, one or more of elasticity image data, strain, or strain rate. The vibration elasticity imaging module 1072 may calculate the vibration elasticity result according to the ultrasound echo data for the vibration elasticity detection. The vibration elasticity result may be, for example, the shear wave elasticity parameter and/or the shear wave trajectory. The shear wave elasticity parameter may include at least one of the propagation velocity of the shear wave, the Young's modulus and the shear modulus. In some embodiments, the data processor 107 may further include an ultrasound image generation module (not shown in the figure) that may generate various ultrasound images, such as B-mode images, according to ultrasound echo data for the strain detection.

The display device 108 may receive various visualization data output by the data processor 107, and displays various images, graphics, charts, text or data on the display interface, including various elasticity parameters, various elasticity images and/or various ultrasound images.

In the embodiments of the present disclosure, the ultrasound probe may be vibrated according to the vibration control sequence under the drive of the vibrator. On the one hand, mechanical vibration is used to replace the manual pressing, which improves the consistency of the pressure and ensures the repeatability and stability of the imaging. On the other hand, the vibration elasticity detection may be performed through the vibration of the ultrasound probe. Therefore, it will no longer be necessary to switch into a single-element probe in order to perform the vibration elasticity detection. Not only can the strain distribution in the region of interest be obtained, but also the elasticity value at the sampling gate can be quantitatively detected. In one embodiment, the vibration control sequence V1 and the vibration control sequence V2 in FIG. 2c, FIG. 2d and FIG. 2e may be the same or different. For example, the pulse width of the vibration control sequence V1 may be longer than the pulse width of the vibration control sequence V2.

Figure 3:
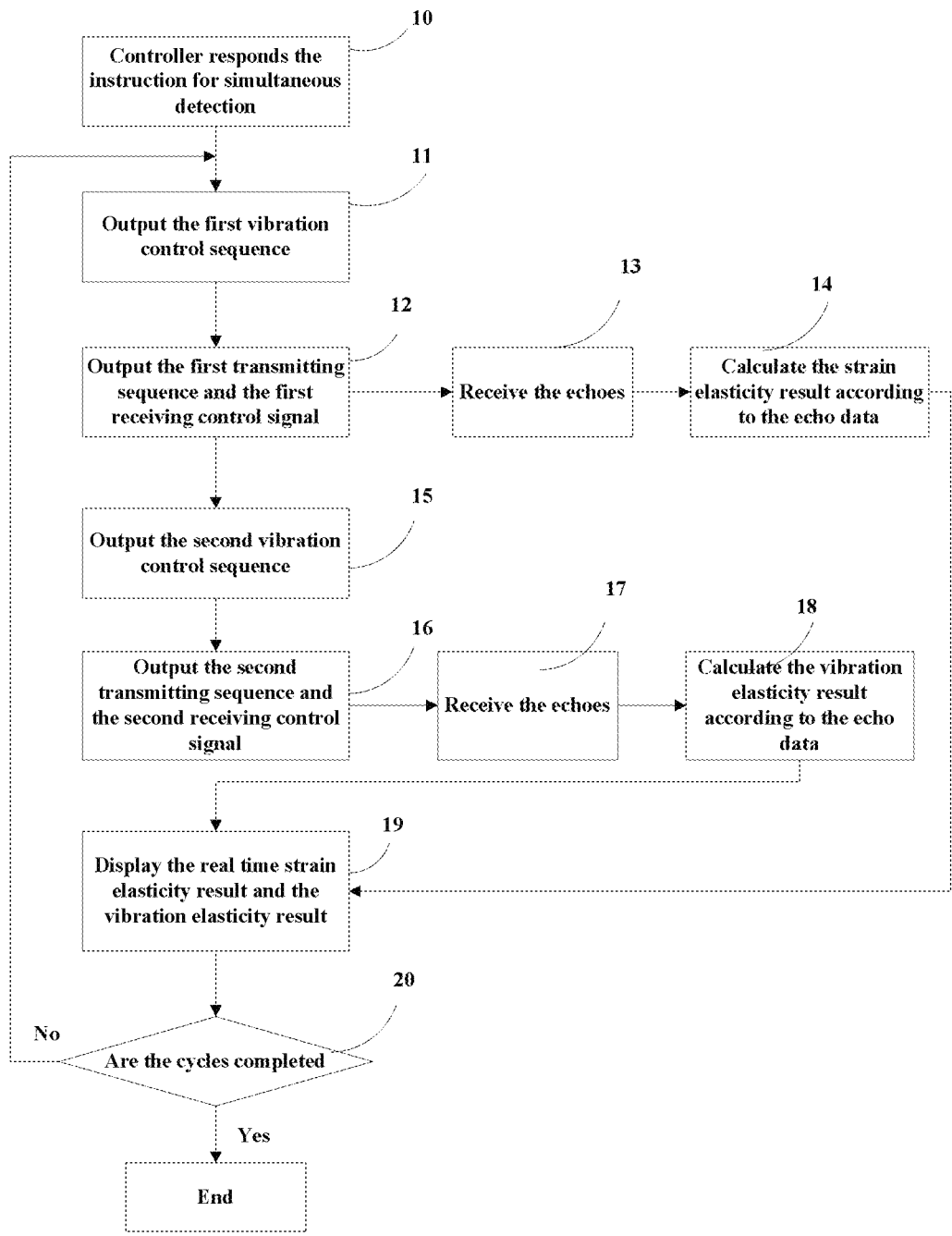
FIG. 3 is a flow chart of simultaneously performing the strain elasticity detection and the vibration elasticity detection in one embodiment.

In the following, the control and processing process will be illustrated through an example in which the vibration corresponding to the ultrasound waves for the strain detection transmitted by the ultrasound probe and the vibration corresponding to ultrasound waves for the shear wave detection are not the same one vibration, as shown in FIG. 3.

In step 10, when the user desires to obtain the strain-type elasticity result and the vibration elasticity result at the same time, the user can input the simultaneous detection instruction through the input device, so as to enter the mode of simultaneously performing the strain detection and the vibration elasticity detection. Response to this instruction, the controller may, in step 11, control the vibration controller to output the first vibration control sequence. The first vibration control sequence may set the parameters such as the waveform, frequency, amplitude, duration or the like of the vibration of the vibrator when detecting the tissue strain. For example, the first vibration control sequence may set a sinusoidal vibration waveform with a frequency of 2 Hz, an amplitude of 0.5 mm and a duration of 2 s.

The vibrator may start the first vibration according to the waveform, frequency and amplitude set by the first vibration control sequence, and end the first vibration according to the duration set by the first vibration control sequence.

In step 12, the controller may control the transmitting/receiving controller to output the first transmitting sequence group and the first receiving control signal. The ultrasound probe may transmit the ultrasound waves and receive the echoes according to the first transmitting sequence group and the first receiving control signal.

In step 13, the echoes may be received, and the echo processing device may process the echo data.

In step 14, the strain elasticity imaging module may calculate the strain elasticity result according to the echo data.

Figure 4:
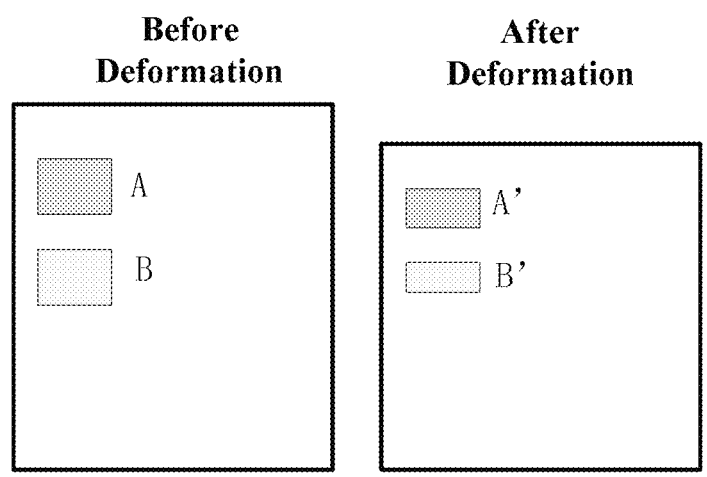
FIG. 4 is a schematic diagram of the displacement detection during the strain elasticity imaging.

The strain elasticity imaging module may determine the location of the region of interest after the tissue is deformed according to two frames of ultrasound echo data before and after the tissue is deformed. There are many methods for calculating the displacement, such as block-matching method. As shown in FIG. 4, based on the two frames of echo data before and after the deformation, the data A and B of a certain region of interest in one of the frames may be selected, and the positions A' and B' of the data that most match the data A and B may be searched in another frame. It may be considered that the region of interest has been moved to the positions, and the position difference between the two frames may be the displacement of the region of interest.

After obtaining the displacement, the strain M in the region of interest may be calculated according to the definition of strain, namely:

$$M=\Delta L/L$$

Where L is the length of the region of interest before the tissue is deformed, and $\Delta L$ is the length change of the region of interest after the tissue is deformed.

In one embodiment, the strain elasticity imaging module may also generate a strain elasticity image of the region of interest according to the strain. According to Hooke's law, stress=strain*Young's modulus. The Young's modulus is a common physical quantity that reflects the hardness of the tissue. Therefore, under a certain pressure, the harder the tissue, the smaller the strain, and the softer the tissue, the greater the strain. When the probe contacts the tissue well, it can be considered that the force uniformly acts on the tissue. Therefore, the strain distribution image can reflect the difference in the hardness of the tissues.

In step 15, after the first vibration is completed, the controller may control the vibration controller to output the second vibration control sequence. The second vibration control sequence may set the parameters such as the waveform, frequency, amplitude, duration or the like of the vibration of the vibrator when detecting the shear wave. For example, the second vibration control sequence may set a sinusoidal vibration waveform with a frequency of 50 Hz, an amplitude of 1 mm and a duration of one cycle.

The vibrator may start the second vibration according to the waveform, frequency and amplitude set by the second vibration control sequence, and end the second vibration according to the duration set by the second vibration control sequence.

In addition to causing the tissue deformation when the vibrator vibrates, due to the adhesion between the tissues, the vibrator may also generate the shear wave that propagates to the depth of the tissue. When the shear wave propagates through, the tissue at the corresponding position will be displaced. After the shear wave propagates through, the displacement will gradually decrease and disappear.

In step 16, the controller may control the transmitting/receiving controller to output the second transmitting sequence group and the second receiving control signal. The ultrasound probe 101 may transmit the ultrasound wave 1091 and receives the echoes according to the second transmitting sequence group and the second receiving control signal. In order to detect the shear wave, the ultrasound probe may transmit the ultrasound wave into the tissue and receive the echoes for a period of time.

In step 17, the echoes may be received, and the echo processing device may process the echo data.

In step 18, the vibration elasticity imaging module may calculate the vibration elasticity result according to the echo data. The vibration elasticity result may be the shear wave elasticity parameter, such as the shear wave propagation velocity, the Young's modulus and/or the shear modulus value. Alternatively, the vibration elasticity result may be the shear wave trajectory. For example, the vibration elasticity result may be calculated by the following methods.

Figure 5:
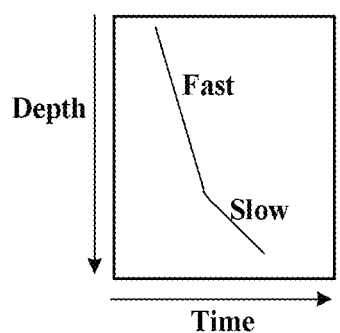
FIG. 5 is a schematic diagram of the propagation trajectory of the shear wave obtained in one embodiment.

The vibration elasticity imaging module may calculate the displacement of a certain point on the shear wave propagation path according to the received echo signals. When the displacement of this point is the largest, it may be considered that the shear wave has reached this point. The propagation path or trajectory of the shear wave may be determined by the times when the shear wave reaches the points. Thereby, the shear wave trajectory may be drawn, as shown in FIG. 5. According to the shear wave trajectory, the slopes at the points on the propagation path of the shear wave may be obtained. The slope may represent the propagation velocity of the shear wave.

For an isotropic elastomer, the shear wave propagation velocity has the following approximate relationship with the Young's modulus and the shear modulus:

$$E=3\rho c^2=3G$$

Where c represents the shear wave velocity, ρ represents the tissue density, E represents the Young's modulus of the tissue, and G represents the shear modulus of the tissue. Normally, the value of ρ may be the value of the density of water. Therefore, when the shear wave propagation velocity is obtained, other elasticity related parameters, such as the Young's modulus or the shear modulus, may be calculated.

Figure 6A:
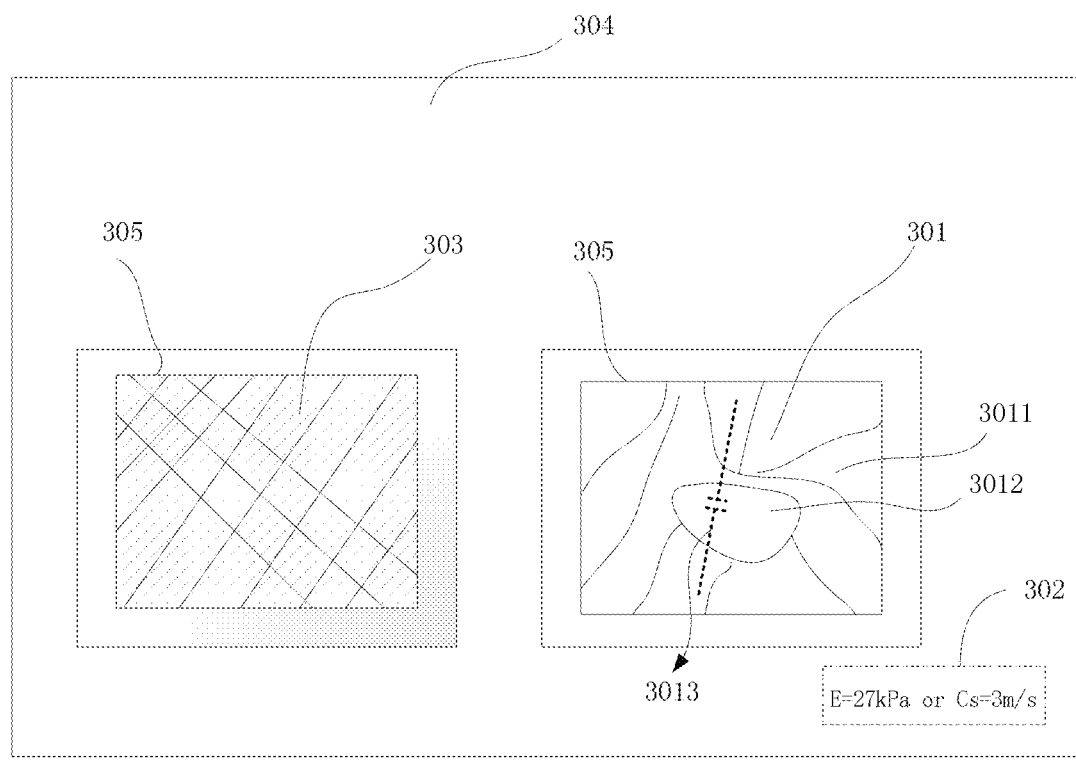
FIGS. 6a-6c are schematic diagrams showing the strain elasticity detection result and the vibration elasticity detection result simultaneously.
Figure 6B:
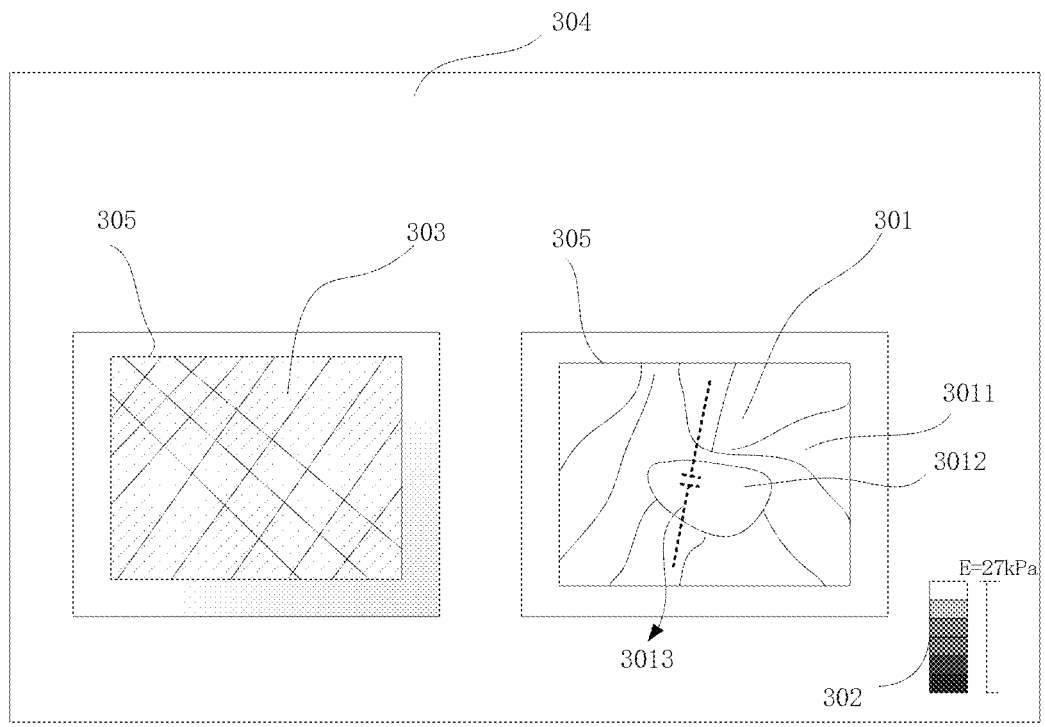
Figure 6C:
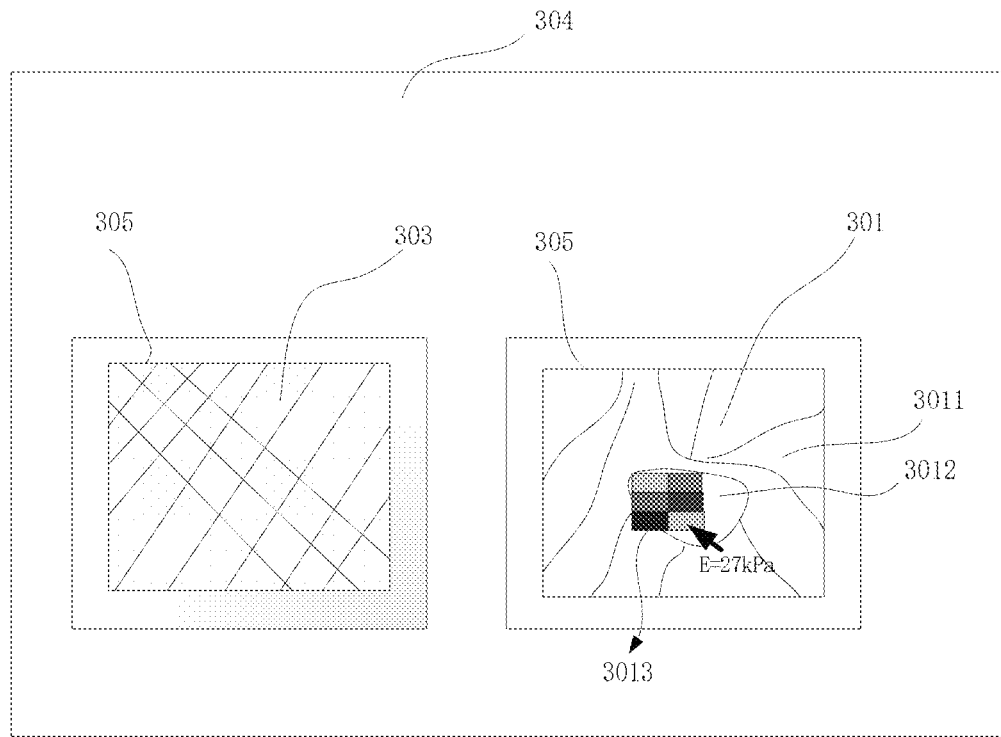

In step 19, the real-time strain elasticity result and the vibration elasticity result may be displayed. For example, the display device may simultaneously display the strain elasticity result and the vibration elasticity result on the display interface. As shown in FIGS. 6a, 6b and 6c, on the display interface 304, the strain elasticity result may be presented in the form of strain distribution image 301. In the strain distribution image 301, the tissue 3011 with the first hardness property and the tissue 3012 with the second hardness property may be marked with different colors, gray levels or filling forms. Furthermore, the sampling gate 3013 may be displayed in the strain distribution image 301. The tissue with the first hardness property and the tissue with the second hardness property may have completely different pixel attributes on the strain distribution image, which may be distinguished in the strain distribution image. The elasticity values in the tissue with the first hardness property and the tissue with the second hardness property may be different or the same. However, for the tissue with the first hardness property and the tissue with the second hardness property, as well as any area within them, no quantitative elasticity measurement results can be obtained in the strain distribution image. In this embodiment, by performing the vibration elasticity detection while measuring the strain, the vibration elasticity of a certain area in the strain distribution image may be measured. The vibration elasticity result at the sampling gate may be displayed in the display area 302. The vibration elasticity result may be presented in various ways. In FIG. 6a, the vibration elasticity result may be presented in number, such as E=27 kPa or Cs=3 m/s. In FIG. 6b, the vibration elasticity result may be represented by filled color or color bar. For example, a scaled color bar may be displayed in the elasticity display area to show the quantitative analysis of the hardness change of the sampling gate in the measuring depth direction. In the figure, the sampling gate is in the tissue with the second hardness property. Alternatively, the sampling gate may be in the tissue with the first hardness property. The position of the sampling gate may be freely selected by the user. The sampling gate may also be represented by a box, so as to represent the vibration elasticity result in the box. The mean value, mean square deviation, variance or other statistics of the elasticity measurement results at the points in the box may be calculated to represent the elasticity measurement result corresponding to the entire box, as shown in FIG. 6c.

In this embodiment, when the ultrasound probe transmit the ultrasound waves for the strain detection and the ultrasound waves for the vibration elasticity detection in turn for different vibrations, that is, when performing periodic detection, the strain elasticity imaging module and the vibration elasticity imaging module may perform the real-time calculation according to the received ultrasound echo data, and the display device may display the real-time updated strain elasticity result and vibration elasticity result in the display interface.

In some embodiments, the data processor may also generate the ultrasound image, such as a B-mode image or a C-mode image, according to the ultrasound echo data for the strain detection. As shown in FIGS. 6a-6c, the display device may also simultaneously display the ultrasound image 303 on the display interface. The ultrasound image 303 and the strain distribution image 301 may be displayed side by side or in a stacked manner. Alternatively, the ultrasound image 303 may cover a part of the strain distribution image 301, or vice versa. The region of interest 305 may be selected in the ultrasound image 303, and the strain distribution image 301 of the region of interest 305 may be displayed in the strain distribution image area.

In step 20, it may be determined whether the cycles are completed. If yes, the detection may be ended. Otherwise, it may be returned to step 11 to start the next cycle of detection. Each time the detection is completed, the displayed strain elasticity result and vibration elasticity result may be updated in real time. The number of the cycles may be set as one or more times as needed.

In the steps above, in one cycle, it may also be possible that the shear wave detection is performed first, and then the strain elasticity detection is performed.

In addition, in one embodiment, the vibration of the vibrator and the transmitting of the ultrasound waves by the ultrasound probe may not be performed simultaneously, but be performed sequentially. For example, the controller may first control the ultrasound probe to transmit the ultrasound waves, and then control the vibrator to vibrate. In this case, the echo data used in the following processing is the echo data after the vibration started. Therefore, in this case, the ultrasound probe may transmit the ultrasound waves for a period of time according to the transmitting interval set by the transmitting sequence group, such as until the end of the vibration of the ultrasound probe. When detecting shear waves, the ultrasound waves may be transmitted for a longer time.

In one embodiment, the vibration control sequences for the first vibration and the second vibration may also be the same. In one embodiment, the frequency of the vibration for detecting the shear wave may be greater than the frequency of the vibration for detecting the tissue deformation.

Figure 7:
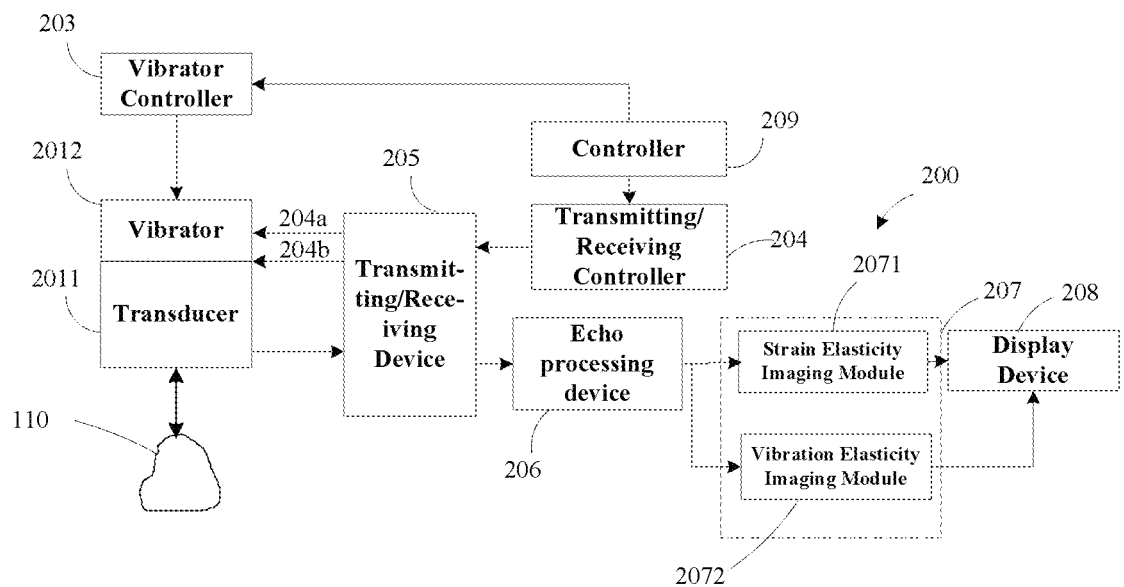
FIG. 7 is a schematic block diagram of the ultrasound elasticity measurement device in another embodiment.
Figure 8:
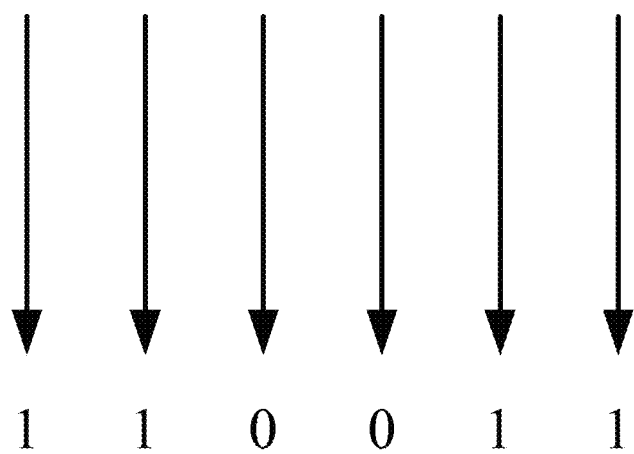
FIG. 8 is a schematic diagram of distinguishing and identifying the sequence in one embodiment.

Referring to FIG. 7, an ultrasound elasticity measurement device 200 may include an ultrasound probe 201, a vibrator 202, a vibration controller 203, a transmitting/receiving controller 204, a transmitting/receiving device 205, an echo processing device 206, a data processor 207, a display device 208 and a controller 209. The connection relationship of the components may be the same as that in the embodiment above. The difference is that when the transmitting/receiving controller 204 generates the transmitting sequence group and receiving control signal, it distinguishes the echo data for detecting the tissue deformation and the echo data for detecting the shear wave by marks in the sequences. For example, the transmitting/receiving controller 204 may output a transmitting sequence group 204a to the ultrasound probe. The transmitting sequence group may set 6 elements for transmitting the ultrasound waves. In the transmitting sequence group 204a, the first and second sequences may be marked with 1, the third and fourth sequences may be marked with 0, and the fifth and sixth sequences may be marked with 1, as shown in FIG. 8. The sequences marked with 1 may be used to transmitting the ultrasound waves for detecting the tissue stain, while the sequences marked with 0 may be used to transmitting the ultrasound wave for detecting the shear wave. The receiving control signal 204b output by the transmitting/receiving controller 204 to the ultrasound probe may also be marked similarly. When the corresponding elements receive the echoes, the echo data may be marked according to the mark of the received control signal. In this case, the ultrasound probe may simultaneously transmit the ultrasound wave for the strain detection and the ultrasound wave for the shear wave detection for the same vibration, and the received echo data may include both ultrasound echo data for the strain detection and the ultrasound echo data for the vibration elasticity detection that have different marks. The data processor may perform different processing on them according to the different marks. For the echo data marked with 1, the strain elasticity imaging module 2071 may calculate the strain according to them. For the echo data marked with 0, the vibration elasticity imaging module 2072 may calculate the vibration elasticity result according to them.

Those skilled in the art should understand that the sequence for detecting the tissue strain marked with 1 may alternatively be marked with 0 or other mark, and the sequence for detecting the shear waves may alternatively be marked with 1 or other mark. Alternatively, one of the two sequences for detecting the tissue strain and detecting the shear waves may be marked, while the other not. Alternatively, the transmitting sequence may not be marked, while the receiving control signal may be marked. In short, it may be possible as long as it can be identified which is the ultrasound echo data for the strain detection and which is the ultrasound echo data for the shear wave detection in the echo data.

Figure 9:
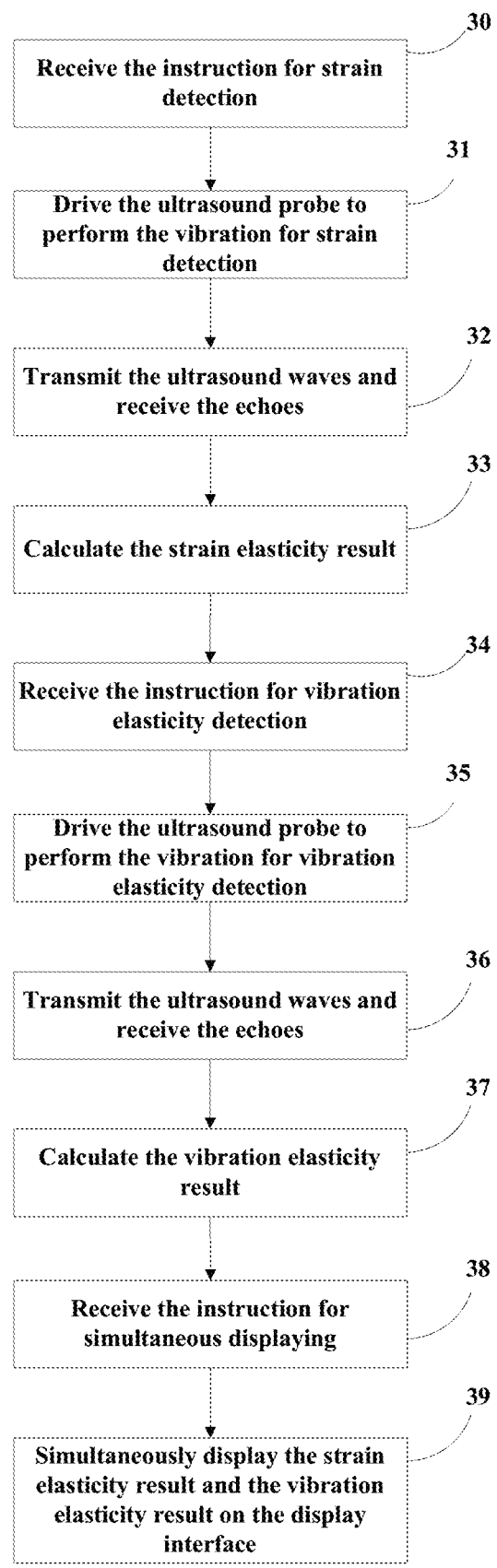
FIG. 9 is a flowchart for simultaneously displaying the strain elasticity result and the vibration elasticity result in another embodiment.

In one embodiment, the user may input the detection instruction twice successively. The flow chart is shown in FIG. 9, which may include the following steps.

In step 30, the instruction for performing the strain detection input by the user may be received, so as to enter the strain detection mode.

In step 31, the vibration controller may output the vibration control sequence for the strain detection to the vibrator. The vibrator may drive the transducer of the ultrasound probe to vibrate according to the vibration control sequence for the strain detection. The vibration may cause the biological tissue to deform when the ultrasound probe contacts the biological tissue, thereby the strain detection may be performed.

In step 32, the transmitting/receiving controller may output the transmitting sequence group and the receiving control signal to the ultrasound probe. Part or all of the multiple elements of the ultrasound probe may transmit the ultrasound waves to the biological tissues in the region of interest according to the transmitting sequence group, and part or all of the multiple elements of the ultrasound probe may receive the echoes of the ultrasound waves according to the received control signal to obtain the ultrasound echo data for the strain detection.

In step 32, the data processor may calculate the strain elasticity result according to the ultrasound echo data for the strain detection.

In step 34, the instruction for performing the vibration elasticity detection input by the user may be received, so as to enter the vibration elasticity detection mode.

In step 35, the vibration control sequence for the vibration elasticity detection may be output to the vibrator. The vibrator may drive the transducer of the ultrasound probe to vibrate according to the vibration control sequence for the vibration elasticity detection. The vibration may generate the shear wave in the biological tissue that propagates toward the depth of the tissue.

In step 36, the transmitting sequence group and the receiving control signal may be output to the ultrasound probe. Part or all of the multiple elements of the ultrasound probe may transmit the ultrasound waves to the biological tissues in the region of interest according to the transmitting sequence group, and par or all of the multiple elements of the ultrasound probe may receive the echoes of the ultrasound waves according to the received control signal to obtain the ultrasound echo data for the vibration elasticity detection.

In step 37, the data processor may calculate the vibration elasticity result according to the ultrasound echo data for the vibration elasticity detection.

In step 38, the instruction for simultaneous displaying input by the user may be received.

In step 39, the display device may simultaneously display the strain elasticity result and the vibration elasticity result on the display interface.

In one embodiment, it may also be possible that the vibration elasticity detection may be performed first, and then the strain detection may be performed. Thereafter, the strain elasticity result and the vibration elasticity result may be displayed simultaneously on the display interface.

In this embodiment, in step 31, the vibrator is used to drive the ultrasound probe to vibrate to cause the deformation of the biological tissue. In other embodiment, the user may also manually press the tissue to cause the tissue to deform for subsequent strain detection.

In one embodiment, the ultrasound probe may further include a pressure sensor. The output end of the pressure sensor may be connected to the data processor. The pressure sensor may sense the pressure. For example, the pressure sensor may detect the driving force of the vibrator to the transducer or the pressure of the probe to the tissue, and feedback the sensed pressure to the data processor. The data processor may normalize the strains detected at different times according to the pressure. For example, at time t1, the corresponding strain is S1 and the pressure is about F1, and at time t2, the corresponding strain is S2 and the pressure is about F2. Therefore, the strain at time 2 may be normalized as $S2\_new=S2*F1/F2$.

In one embodiment, the ultrasound elasticity measurement device may not use the controller to control the output sequence of the vibration controller and the transmitting/receiving controller, but may connect the transmitting/receiving controller with the vibration controller. When the vibration controller outputs the vibration control sequence, the transmitting/receiving controller may correspondingly output the transmitting sequence group and receiving control signals.

The functions in the present disclosure may be implemented by the program described in the embodiments above or by hardware, such as by an application specific integrated circuit built by gate circuits. Those skilled in the art can understand that the various programs in the embodiments above may be stored in a computer-readable storage medium. The storage medium may include a read-only memory, a random access memory, a magnetic disk or an optical disk, etc. The data processor may achieve the functions above by executing the programs.

This disclosure has been made with reference to various exemplary embodiments. However, those skilled in the art will recognize that changes and modifications may be made to the exemplary embodiments without departing from the scope of the present disclosure. For example, various operational steps, as well as components for carrying out operational steps, may be implemented in alternate ways depending upon the particular application or in consideration of any number of cost functions associated with the operation of the system, e.g., one or more of the steps may be deleted, modified, or combined with other steps.

Additionally, as will be appreciated by one of ordinary skill in the art, principles of the present disclosure may be reflected in a computer program product on a computer-readable storage medium having computer-readable program code means embodied in the storage medium. Any tangible, non-transitory computer-readable storage medium may be utilized, including magnetic storage devices (hard disks, floppy disks, and the like), optical storage devices (CD-ROMs, DVDs, Blu-Ray discs, and the like), flash memory, and/or the like. These computer program instructions may be loaded onto a general purpose computer, special purpose computer, or other programmable data processing apparatus to produce a machine, such that the instructions that execute on the computer or other programmable data processing apparatus create means for implementing the functions specified. These computer program instructions may also be stored in a computer-readable memory that can direct a computer or other programmable data processing apparatus to function in a particular manner, such that the instructions stored in the computer-readable memory produce an article of manufacture, including implementing means that implement the function specified. The computer program instructions may also be loaded onto a computer or other programmable data processing apparatus to cause a series of operational steps to be performed on the computer or other programmable apparatus to produce a computer-implemented process, such that the instructions that execute on the computer or other programmable apparatus provide steps for implementing the functions specified.

While the principles of this disclosure have been shown in various embodiments, many modifications of structure, arrangements, proportions, elements, materials, and components, which are particularly adapted for a specific environment and operating requirements, may be used without departing from the principles and scope of this disclosure. These and other changes or modifications are intended to be included within the scope of the present disclosure.

The foregoing specification has been described with reference to various embodiments. However, one of ordinary skill in the art will appreciate that various modifications and changes can be made without departing from the scope of the present disclosure. Accordingly, this disclosure is to be regarded in an illustrative rather than a restrictive sense, and all such modifications are intended to be included within the scope thereof. Likewise, benefits, other advantages, and solutions to problems have been described above with regard to various embodiments. However, benefits, advantages, solutions to problems, and any element(s) that may cause any benefit, advantage, or solution to occur or become more pronounced are not to be construed as a critical, a required, or an essential feature or element. As used herein, the terms "comprises," "comprising," and any other variation thereof, are intended to cover a non-exclusive inclusion, such that a process, a method, an article, or an apparatus that comprises a list of elements does not include only those elements but may include other elements not expressly listed or inherent to such process, method, system, article, or apparatus. Also, as used herein, the terms "coupled," "coupling," and any other variation thereof are intended to cover a physical connection, an electrical connection, a magnetic connection, an optical connection, a communicative connection, a functional connection, and/or any other connection.

Those having skill in the art will appreciate that many changes may be made to the details of the above-described embodiments without departing from the underlying principles of the disclosure. The scope of the present disclosure should, therefore, be determined only by the following claims.

The invention claimed is:

1. An ultrasound elasticity measurement device, comprising:
an ultrasound probe comprising a vibrator and a transducer, wherein the transducer comprises multiple elements;
a transmitting/receiving controller configured to generate a first transmitting sequence group and a first receiving control signal, and a second transmitting sequence group and a second receiving control signal, and output the first and second transmitting sequence groups and the first and second receiving control signals to the ultrasound probe;
a vibration controller connected to the vibrator and configured to generate a first vibration control sequence for strain detection and a second vibration control sequence for vibration elasticity detection and output the first and second vibration control sequences to the vibrator, wherein the first vibration control sequence lasts for a first time period and the second vibration control sequence lasts for a second time period, wherein:
the vibrator obtains the first and second vibration control sequences and drives the transducer to vibrate according to the first vibration control sequence to generate deformations of a biological tissue and according to the second vibration control sequence to generate shear waves that propagate to inside of the biological tissue in a region of interest,
the first transmitting sequence group controls a first group of the multiple elements to transmit a first ultrasound wave to the biological tissue to detect the deformation of the biological tissue, and the second transmitting sequence group controls a second group of the multiple elements to transmit a second ultrasound wave to a position where the shear waves passes,
the first receiving control signal controls a third group of the multiple elements to receive echoes of the first ultrasound wave to obtain a first ultrasound echo data for the strain detection, and the second receiving control signal controls a fourth group of the multiple elements to receive echoes of the second ultrasound wave to obtain a second ultrasound echo data for the vibration elasticity detection, wherein the first transmitting sequence group and the first receiving control signal are applied and ended within the first time period, and the second transmitting sequence group and the second receiving control signal are applied within the second time period and ended outside of the second time period,
wherein a time period between an end of the first receiving control signal and a start of the second transmitting sequence group is greater than a time period between an end of the first vibration control sequence and a start of the second vibration control sequence, or
wherein a time period between an end of the second receiving control signal and a start of the first transmitting sequence group is less than a time period between an end of the second vibration control sequence and a start of the first vibration control sequence; and
a data processor configured to simultaneously calculate a strain elasticity result according to the first ultrasound echo data for the strain detection and a vibration elasticity result according to the second ultrasound echo data for the vibration elasticity detection.

2. The device of claim 1, wherein a second parameter of the second vibration control sequence for the vibration elasticity detection and a first parameter of the first vibration control sequence for the strain detection are different.

3. The device of claim 1, wherein the second transmitting sequence group starts after a start of the second time period.

4. The device of claim 1, wherein, the received second ultrasound echo data is marked for the vibration elasticity detection and the received first ultrasound echo data is marked for the strain detection with different marks.

5. The device of claim 1, further comprising a controller respectively connected to the vibration controller and the transmitting/receiving controller and configured to control output sequences of the first and second transmitting sequence groups and the first and second receiving control signals and the first and second vibration control sequences.

6. The device of claim 1, wherein the transmitting/receiving controller is connected with the vibration controller and configured to output the first and second transmitting sequence groups and the first and second receiving control signals when the vibration controller outputs the first and second vibration control sequences.

7. The device of claim 1, further comprising a display device configured to simultaneously display the strain elasticity result and the vibration elasticity result on a display interface of the display device.

8. The device of claim 7, wherein the data processor is further configured to generate an ultrasound image according to the first ultrasound echo data for the strain detection, and the display device is further configured to display the ultrasound image.

9. An ultrasound elasticity measurement method, comprising:
receiving an instruction for simultaneously performing a strain detection and a vibration elasticity detection to enter a mode of simultaneously performing the strain detection and the vibration elasticity detection;
outputting a first vibration control sequence and a second vibration control sequence to a vibrator, wherein the vibrator drives a transducer of an ultrasound probe to vibrate according to the first and second vibration control sequences, wherein the first vibration control sequence lasts for a first time period and the second vibration control sequence lasts for a second time period, and wherein the vibration causes a biological tissue to deform when the ultrasound probe contacts the biological tissue and generates a shear wave that propagates to inside of the biological tissue;
outputting a first transmitting sequence group and a first receiving control signal, and a second transmitting sequence group and a second receiving control signal to the ultrasound probe;
controlling a first group of multiple elements of the ultrasound probe according to the first transmitting sequence group to transmit a first ultrasound wave to the biological tissue in a region of interest, and controlling a second group of the multiple elements according to the first receiving control signal to receive first echoes of the first ultrasound wave to obtain a first ultrasound echo data for the strain detection;
controlling a third group of the multiple elements of the ultrasound probe according to the second transmitting sequence group to transmit a second ultrasound wave to the biological tissue in the region of interest, and controlling a fourth group of the multiple elements according to the second receiving control signal to receive second echoes of the second ultrasound wave to obtain a second ultrasound echo data for the vibration elasticity detection, wherein the first transmitting sequence group and the first receiving control signal are applied and ended within the first time period, and the second transmitting sequence group and the second receiving control signal are applied within the second time period and ended outside of the second time period,
wherein a time period between an end of the first receiving control signal and a start of the second transmitting sequence group is greater than a time period between an end of the first vibration control sequence and a start of the second vibration control sequence, or
wherein a time period between an end of the second receiving control signal and a start of the first transmitting sequence group is less than a time period between an end of the second vibration control sequence and a start of the first vibration control sequence; and
simultaneously calculating, by a data processor, a strain elasticity result according to the first ultrasound echo data for the strain detection and a vibration elasticity result according to the second ultrasound echo data for the vibration elasticity detection.

10. The method of claim 9, further comprising simultaneously displaying the strain elasticity result and the vibration elasticity result on a display interface.

11. The method of claim 9, wherein the second transmitting sequence group starts after a start of the second time period.

12. An ultrasound elasticity measurement method, comprising:
generating a deformation in a biological tissue by a first vibration under control of a first vibration control sequence lasting for a first time period;
generating in the biological tissue a shear wave propagating to inside of the biological tissue by a second vibration under control of a second vibration control sequence lasting for a second time period;
transmitting a first ultrasound wave to the biological tissue through an ultrasound probe and receiving first ultrasound echoes through the ultrasound probe to obtain first ultrasound echo data for strain detection, wherein the transmitting of the first ultrasound wave and the receiving of first ultrasound echoes are started and ended within the first time period;
transmitting a second ultrasound wave to the biological tissue through the ultrasound probe to track a propagation of the shear wave and receiving second ultrasound echoes through the ultrasound probe to obtain a second ultrasound echo data for vibration elasticity detection, wherein the transmitting of the first ultrasound wave and the receiving of first ultrasound echoes are started within the second time period and ended outside of the second time period,
wherein a time period between an end of the first receiving control signal and a start of the second transmitting sequence group is greater than a time period between an end of the first vibration control sequence and a start of the second vibration control sequence, or
wherein a time period between an end of the second receiving control signal and a start of the first transmitting sequence group is less than a time period between an end of the second vibration control sequence and a start of the first vibration control sequence;
calculating a vibration elasticity result according to the second ultrasound echo data for the vibration elasticity detection;
calculating a strain elasticity result according to the first ultrasound echo data for the strain detection; and
simultaneously displaying the strain elasticity result and the vibration elasticity result.

* * * * *